(12) United States Patent
Blackman et al.

(10) Patent No.: US 7,111,350 B2
(45) Date of Patent: Sep. 26, 2006

(54) MULTI-PART SINGLE-USE TOOTHBRUSH SYSTEM

(76) Inventors: Clyde Blackman, 1772 Sespe Dr., Ventura, CA (US) 93004; Ray Colletti, 2610 Springbrook Ct., Thousand Oaks, CA (US) 91362

( * ) Notice: Subject to any disclaimer, the term of this patent is extended or adjusted under 35 U.S.C. 154(b) by 0 days.

(21) Appl. No.: 10/769,944

(22) Filed: Feb. 2, 2004

(65) Prior Publication Data
US 2004/0172778 A1    Sep. 9, 2004

Related U.S. Application Data

(63) Continuation-in-part of application No. 10/353,442, filed on Jan. 29, 2003, now abandoned.

(51) Int. Cl.
*A61C 17/34* (2006.01)

(52) U.S. Cl. ............... 15/28; 15/104.93; 15/176.1; 15/22.1

(58) Field of Classification Search ............ 15/28, 15/104.93–104.94, 167.1, 22.1, 176.1, 176.6
See application file for complete search history.

(56) References Cited

U.S. PATENT DOCUMENTS

| | | | | |
|---|---|---|---|---|
| 3,162,876 | A * | 12/1964 | Erickson et al. ............... 15/28 |
| 4,198,171 | A * | 4/1980 | Lampka et al. .............. 401/269 |
| 4,811,445 | A * | 3/1989 | Lagieski et al. ........... 15/104.94 |
| 5,146,643 | A * | 9/1992 | Bojar et al. .................... 15/28 |
| 6,161,244 | A * | 12/2000 | Jeannet et al. .............. 15/167.1 |
| 6,363,568 | B1 * | 4/2002 | Harrison et al. ........... 15/167.1 |
| 6,766,548 | B1 * | 7/2004 | Lukas et al. ................ 15/22.1 |
| 6,792,640 | B1 * | 9/2004 | Lev .............................. 15/28 |
| 2005/0210609 | A1 * | 9/2005 | Zhu .............................. 15/28 |

* cited by examiner

*Primary Examiner*—Gladys JP Corcoran
*Assistant Examiner*—Shay Balsis
(74) *Attorney, Agent, or Firm*—Patrick F. Bright

(57) ABSTRACT

A multi-part single-use toothbrush system includes an electric toothbrush such as a rotary electric toothbrush, a plurality of disposable toothbrush heads, some with one or more tooth-cleaning/preserving substances sufficient for a single use, and each with a connector for attachment to and detachment from the electric toothbrush, a dispenser for holding and dispensing such disposable toothbrush heads, and a plurality of sealed single use capsules each containing a brush head and one or more tooth-cleaning/preserving substances.

9 Claims, 4 Drawing Sheets

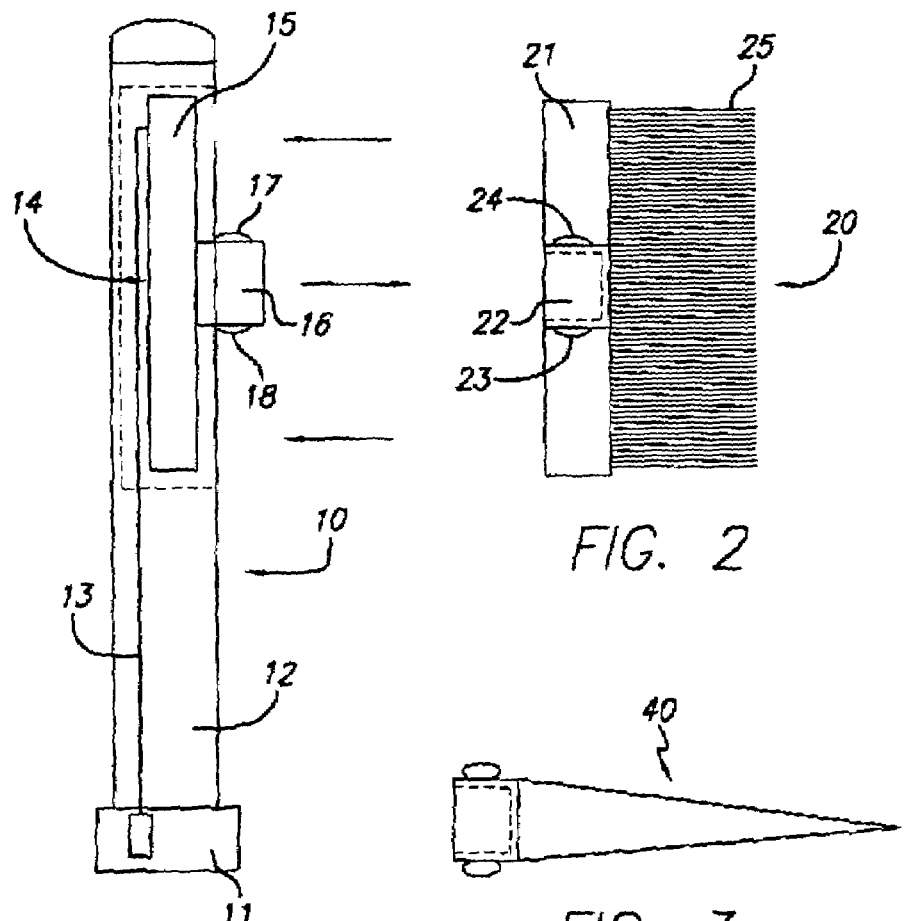
FIG. 2
FIG. 3
FIG. 1
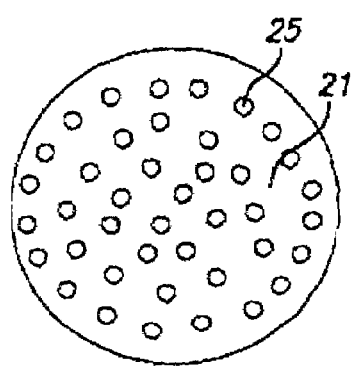
FIG. 5
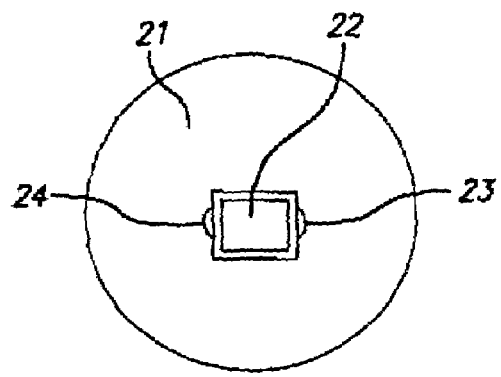
FIG. 4

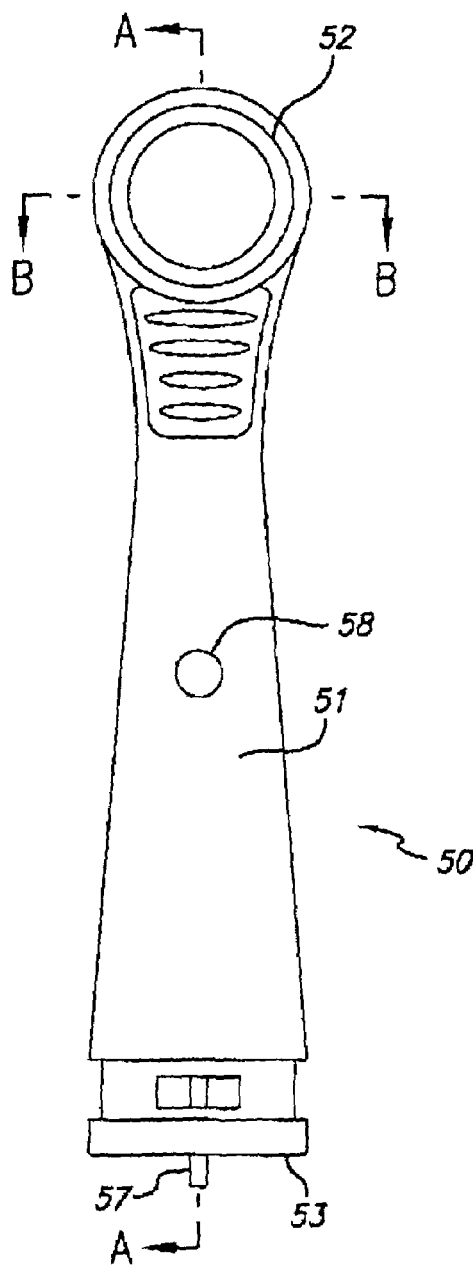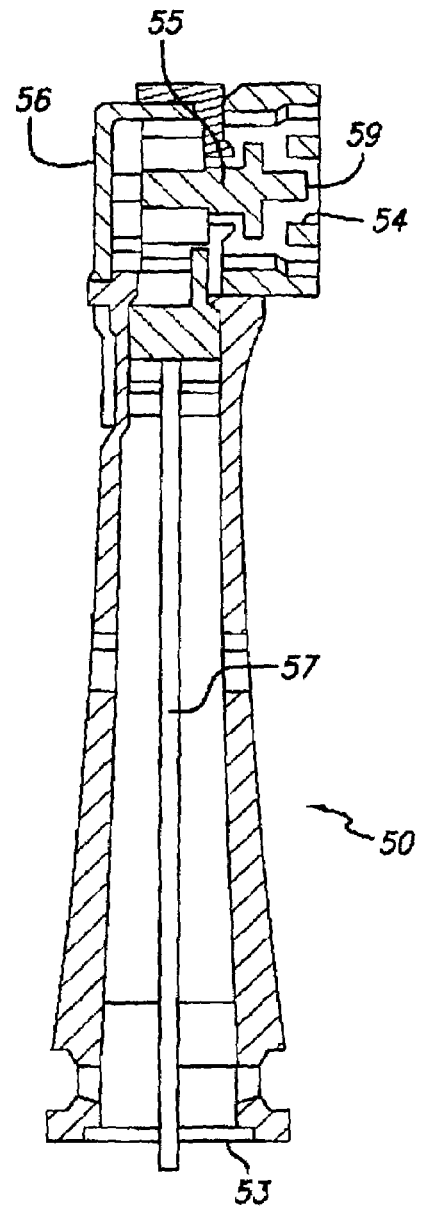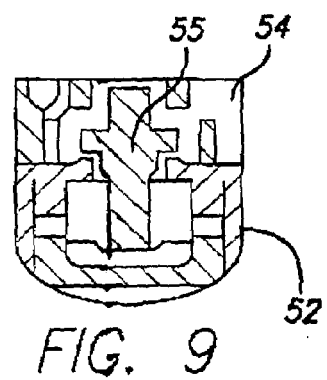
FIG. 7
FIG. 8
FIG. 9

MULTI-PART SINGLE-USE TOOTHBRUSH SYSTEM

This application is a continuation-in-part of U.S. patent application Ser. No. 10/353,442, filed Jan. 29, 2003 now abandoned, in the United States Patent and Trademark Office, and entitled "Multi-Part Single Use Toothbrush System".

This invention relates to a multi-part, single-use, disposable head (may be round in shape), toothbrush system that comprises: an electric toothbrush that may be a rotary or an oscillating electric toothbrush; a toothbrush spindle/neck segment; a disposable toothbrush head with bristles that may bear at least one or more tooth-cleaning/preserving substances sufficient for a single tooth-brushing use, and with a connector for attachment to and detachment from the electric toothbrush; attachment, drive and release mechanisms for the head and spindle/neck segment; a sealed capsule comprising a brush and one or more tooth-cleaning/preserving substances, e.g., dentifrice, and, in some embodiments, a dispenser for holding and dispensing a disposable toothbrush head and one or more tooth-cleaning/preserving substances in combination, or capsules comprising one or more such substances.

The capsules may be made from thermoformed plastic or foil, and may include a single brush head and at least one or more tooth-cleaning/preserving substances. Each capsule may be sealed, and may include moisture and oxygen barriers. In some embodiments, the capsule has a peel-off lid, e.g., a plastic film or foil lid, which also includes moisture and oxygen barriers. The capsule protects the brush head and one or more tooth-cleaning/preserving substances from contamination and environmental damage. The capsule may also function as an applicator to attach the contained brush head and one or more tooth-cleaning/preserving substances to the toothbrush spindle/neck, or as a dentifrice or other tooth-cleaning/preserving substances dispenser, to apply them to brush.

These capsules may be in the shape and size of a brush head. The capsules may be sanitarily filled with one or more tooth-cleaning/preserving substances, e.g., toothpaste, or any type of paste, medicament, polish compound/paste, whitening agent, etc., and, in some embodiments, a brush head, then sealed on the top of the capsule with a barrier film to prevent moisture, air, germs, bacteria, etc. from entering the capsule and to prevent moisture escaping from the capsule. Capsules without a toothbrush head, but with at least one tooth-cleaning/preserving substance, are suitable for single use with all brushes, manual, electric, or otherwise.

The electric toothbrush may, in some embodiments, have replaceable or rechargeable batteries, or both. The toothbrush may also comprise a connector such as a spindle/neck segment to connect to a brush head that rotates or oscillates the brush head, e.g., through about 5° or about 360°, to promote proper oral hygiene, The toothbrush spindle/neck may comprise a male attachment apparatus, a drive spline for the brush disk, and a push button release mechanism to eject a brush head from the spindle/neck. The spindle/neck connects to the base of an electric toothbrush that may comprise an on/off switch, a motor, and batteries.

In some embodiments, the toothbrush head connector, e.g., a male connector, comprises a multi-sided, e.g. six-sided, metal shaft, and a metal, e.g. stainless steel, disk embedded in the head of the spindle/neck segment in some embodiments. The male connector is connected to a drive shaft in the spindle/neck segment in some embodiments. The drive shaft is connected to a motor in the base of the toothbrush. The head connector, e.g., a female connector, may be part of the disk of the brush head, and, where plastic, may be made by injection molding procedures.

In use, the male connector pushes into, and seats in, the female connector located in the brush disk. After use, a user may operate an eject switch on the spindle/neck to detach the brush disk from the male connector. Other dental oral care instruments may be made to attach to the male connector on the toothbrush, such as a flosser, interproximal/ortho brush, prophy cup or some other dental instrument that includes an appropriate connector. The brush or other oral care instrument resides in a sealed capsule until a user removes a top film layer from the capsule, exposing the connector of the brush disk. The connector is pushed/snapped into/onto the complementary connector on the brush disk and the brush is withdrawn from the capsule. A user need not touch the brush or the substances thereon. After withdrawal of the brush head and tooth-cleaning/preserving substances from a capsule, a user can brush their teeth, and then push the eject button on the spindle/neck segment to detach the brush head. In some embodiments using dentifrice alone in a capsule, after removing the capsule cover, a brush may be dipped into the capsule to apply dentifrice to the brush. Advantageously, the system may minimize cross-contamination, while providing a new brush and a pre-measured amount of one or more tooth-cleaning/preserving substances for each brushing.

The toothbrush heads comprise bristles that may be soft, rounded and/or polished. These bristles may be arrayed in a circular or other pattern on a connector, e.g., a plastic disk carrier, for attachment to the rotating or oscillating connector of the electric toothbrush. The disk may be made of any type of plastic such as PP, PET, APET, etc. The heads may carry one or more tooth-cleaning/preserving substances in a quantity sufficient for a single tooth-brushing use, thus eliminating the need for separate toothpaste, or other tooth-cleaning/preserving substances, and the need for dispensers for such substances. In some embodiments, the brush has space between bristles for accommodating a single use quantity of such substances. These substances are released during brushing.

These substances may be contained within the capsule along with the brush. In some embodiments, these substances may include medicaments, bleaching agents, or other compounds. Where the brush disk is attached to the toothbrush neck/spindle segment, the capsule/applicator may be withdrawn from the brush disk; the substances remain on the brush bristles. The toothbrush would then be ready for use. After one use, a brush disk may be discarded.

Many different disk and brush configurations are useful in this system. Examples are a single use flossing attachment, a brush configured for interproximal spaces for orthodontic appliances or bridgework, or a rubber or silicone prophy cup, or another oral/dental care device that can be incorporated with an attachment disk.

Where one or more tooth-cleaning/preserving substances are contained within the brush, the capsule protects the brush from abrasion or other mishandling/rough handling of the brush heads, so that during packaging or otherwise, nothing removes these substances until they contact a material such as saliva, water or mouth rinse which can dissolve and/or release them from the bristles. Since these substances are not chemically bonded to the bristles, they may be removed through contact with water, saliva or physical contact during brushing and thus released on contact with teeth and gums.

In general, a capsule may be filled with a brush head and dentifrice by placing first one or more tooth-cleaning/preserving substances, then a brush head, into a capsule; or by applying such substances to a brush head, placing the substance-loaded head into a capsule, and then placing a closure on the capsule. An alternative for incorporating such substances in the bristles is solvent impregnation and drying. Impregnation may also occur through dipping or spraying. Another alternative for delivering such substances is to include a plurality of hollow bristles, rather than solid bristles, in the brush tip and to draw the dissolved substances into the individual bristles. Another alternative is the use of absorptive bristle materials, or incorporating the substances into the bristles before construction of the brush tip.

In preferred embodiments, the system includes a dispenser for a plurality of capsules/brush heads that releases/dispenses a desired number of capsules/brush heads, preferably one at a time, and holds a plurality of such heads, e.g. heads of the same kind, or heads of different kinds.

This multi-part system may eliminate auto-contamination of toothbrush heads; may eliminate communal contamination of toothpaste; may eliminate damage to gingiva and dental structures, and poor plaque removal, caused by using damaged/old toothbrush bristles; and may provide a practical, workable, and inexpensive alternative to other toothbrush systems. Most toothbrushes are unsuitable to use around bridges or tooth furcations. This system may include a plurality of different brush heads to clean such areas.

BRIEF DESCRIPTION OF THE DRAWINGS

The system can be better understood by reference to the drawings, in which:

FIG. 1 is a side elevation view of an electric toothbrush that forms part of one embodiment of the system;

FIG. 2 shows a side elevation view of a toothbrush head carrying one or more tooth-cleaning/preserving substances such as toothpaste and including a connector for attachment to the electric toothbrush shown in FIG. 1;

FIG. 3 shows a side elevation view of an interproximal brush head with a female snap connector for the electric toothbrush in FIG. 1;

FIG. 4 shows an end elevation view of the rotary brush head shown in FIG. 2;

FIG. 5 shows a front elevation view of the toothbrush head shown in FIG. 2;

FIG. 7 shows a front elevation view of a spindle/neck segment for an electric toothbrush base that includes a connector for a brush head disk and a mechanism for ejecting the brush head disk from the connector;

FIG. 8 is a side elevation view in cross section, taken on lines A—A of FIG. 7, of the spindle/neck segment of FIG. 7;

FIG. 9 is a side elevation view in cross section, taken on line B—B of FIG. 7, of a portion of the spindle/neck segment shown in FIG. 7;

DETAILED DESCRIPTION OF THE DRAWINGS

Figure 6:
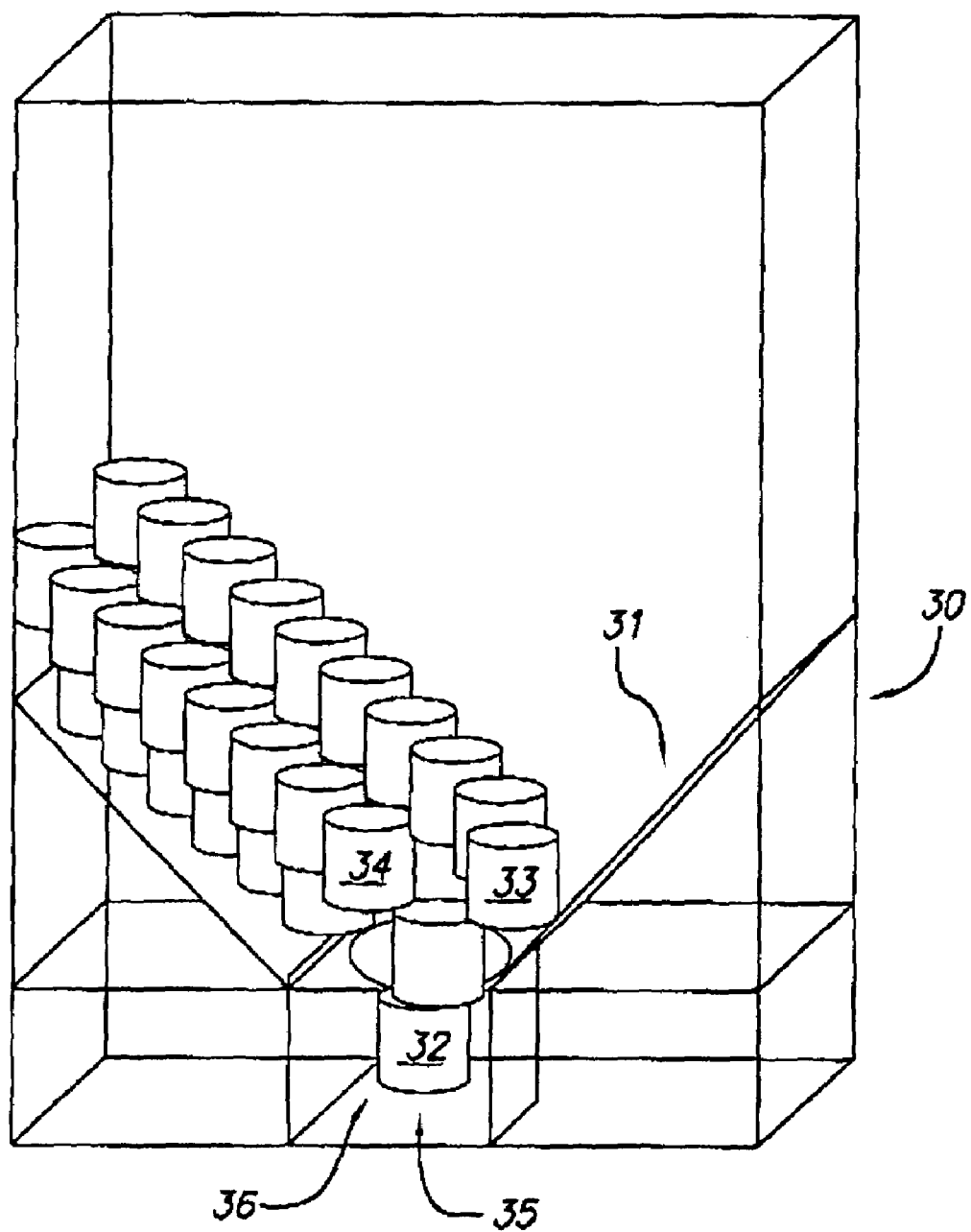
FIG. 6 shows a front perspective view of a dispenser for a plurality of brush heads for use in the system.

FIG. 1 shows electric toothbrush 10 for use in an embodiment of the system. Toothbrush 10 includes twist ring 11 for attaching the toothbrush to a motor (not shown) that oscillates or rotates the toothbrush head connector. Extending from twist ring 11 is brush housing 12, and inside housing 12, rotating shaft arm 13. Arm 13 connects to a base motor (not shown) through twist ring 11. Also connected to arm 13 is rotating snap friction disk plate 15. Attached to plate 15 is male snap friction connector 16 that includes retractable projections 17 and 18 at opposite ends. Bracket 14 holds shaft arm 13 and the parts connected thereto in the desired orientation within housing 12.

FIGS. 2, 4, and 5 show side elevation, rear elevation, and front elevation views, respectively, of brush head 20. Brush head 20 includes base plate 21 with female opening 22 including recesses 23 and 24. These recesses 23 and 24 are complementary in size and shape to projections 18 and 17, respectively, on toothbrush 10, permitting attachment to and detachment from housing 12 after a single use. Connected to plate 21 on the side opposite opening 22 are a plurality of rounded soft bristles 25 that carry, e.g. are impregnated with, one or more substances such as toothpaste.

FIG. 3 shows an interproximal brush head connector 40 for brushing interproximal areas in human teeth. Head 40 attaches to and detaches from connector 16 in the same way as head 20.

FIG. 6 shows brush head dispenser 30, of a four sided container having an internal funneling system 31 that delivers a plurality of brush heads 32, 33 and 34, one at a time, for user access through opening 35 in passageway 36.

FIGS. 7, 8, and 9 show a preferred embodiment of spindle/neck segment 50. The spindle/neck segment 50 includes spindle housing 51 with spindle 57 housed inside housing 51, and brush disk connector 55 linked to spindle 57 to oscillate connector 55 through 360°. Spindle/neck segment 50 includes head member 52, which includes mechanism-linking spindle 57 to oscillating connector 55. Mounted on connector 55 is brush disk 54 (bristles of the brush are omitted for simplification). Connector 55 penetrates into opening 59 in disk 54 to seat brush disk 54 on connector 55. Pushing button 56 detaches brush disk 54 from connector 55.

Figure 10:
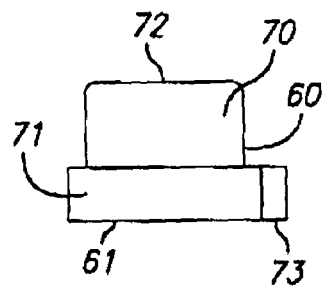
FIGS. 10 and 11 are side elevation and top plan views, respectively, of a capsule, and of the removable top cover for a capsule, for holding a brush head and dentifrice or dentifrice alone.
Figure 11:
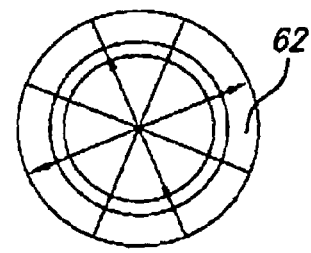

FIG. 10 shows an embodiment of a capsule in frustoconical shape, closed at one end 72, and open at the top. Section 70 of capsule 60 is smaller in cross-section than section 71. Around the opening of capsule 70 is flange 73, which extends beyond the outer surface of section 71. After a brush head disk and dentifrice, or dentifrice alone, are placed within capsule 70, capsule 70 is sealed by sealing lid 62 to flange 73.

Figure 12:
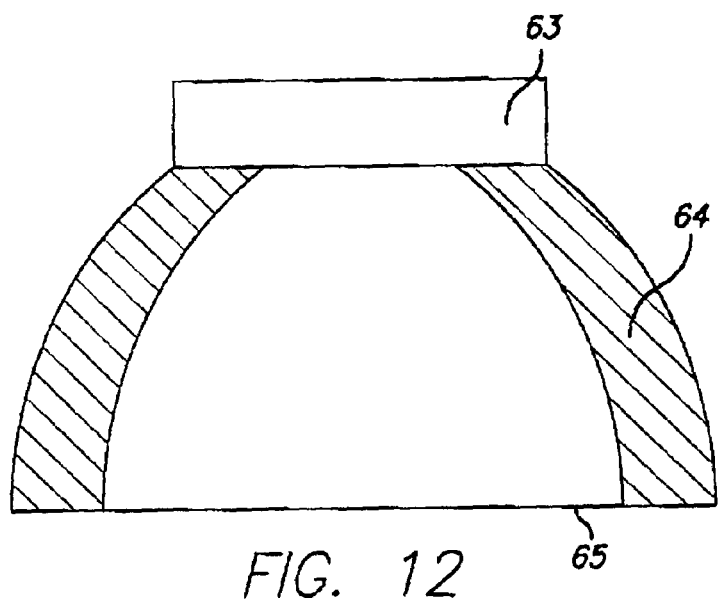
FIGS. 12, 13, and 14 show additional oral treatment devices, namely, a flossing device, a prophy cup, and an angled bristle brush, for attachment to the spindle/neck connector shown in FIG. 7-9.
Figure 13:
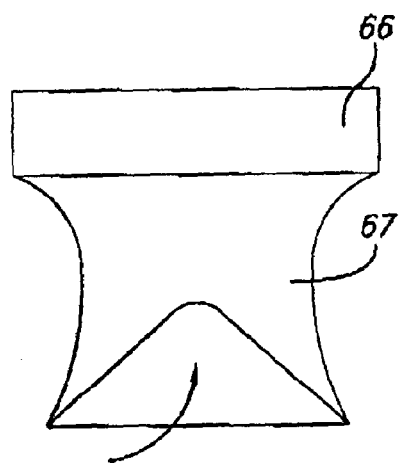
Figure 14:
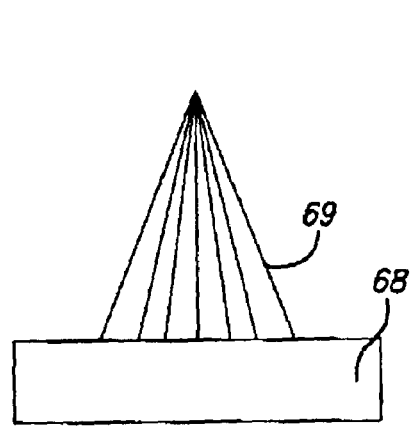

FIGS. 12, 13, and 14 show additional dental devices, other than a brush head, that can be connected to the spindle/neck segment shown in FIGS. 7 and 8. FIG. 12 shows a flossing device with disk 63 connected to arm 64. Across arm 64 is dental floss 65.

FIG. 13 shows a prophy cup with disk 66 attached to cup 67.

FIG. 14 shows a brush for use in proximal areas, including bristle 69, that form a cone shaped array connected to disk 68.

The invention claimed is:

1. A multi-part single-use toothbrush system comprises:
an electric toothbrush including a rotatable or oscillatable segment that includes a first, male connector for a disposable toothbrush head, and a manually-operated ejector mechanism for engaging said head and for positively ejecting said head from said first connector, said male connector and said ejector mechanism being separate elements, and a plurality of disposable, round toothbrush heads, each with bristles forming a rounded profile at the ends of said bristles, said bristles carrying one or more tooth-cleaning/preserving substances sufficient for a single tooth-brushing use, each head including a second, female connector comprising a substantially flat surface with an opening of location, size and shape for attachment to said first, male connector, and for engagement with said elector mechanism upon manual activation of said ejector mechanism to cause positive ejection of said head from attachment to said first connector.

2. The system of claim 1 further comprising a dispenser for holding and dispensing said toothbrush heads or capsules comprising said disposable toothbrush heads, and said one or more tooth-cleaning/preserving substances.

3. The system of claim 2 wherein said first connector can rotate or oscillate a toothbrush head through an arc of about 5° or through an arc of about 360°.

4. The system of claim 1 wherein said first connector can rotate or oscillate a toothbrush head through an arc of about 5° or through an arc of about 360°.

5. The system of claim 1 wherein each of said heads is packaged within an individual, closed capsule, with said substantially flat surface positioned in said capsule to engage said first, male connector upon removal of the closure from said capsule, together with said at least one or more tooth-cleaning/preserving substances, and wherein said first, male connector includes a member that joins to a complementary, female connector on said head.

6. The system of claim 5 further comprising a spindle/neck segment that includes said member and said ejector mechanism for detaching a toothbrush head from said first, male connector.

7. A multi-part single-use toothbrush system comprises:

an electric toothbrush including a rotatable or oscillatable segment that includes a first, male connector for a disposable toothbrush head, and a manually-operated ejector mechanism for engaging said head and for positively ejecting said head from said first, male connector, said male connector and said ejector mechanism being separate elements;

a plurality of disposable toothbrush heads, each including a second, female connector comprising a substantially flat surface with an opening of location, size and shape for attachment to and detachment from said first, male connector, and a plurality of single-use, closed capsules, each capsule containing said disposable, round toothbrush head, each head including bristles and one or more tooth-cleaning/preserving substances sufficient for a single use, with said substantially flat surface positioned in said capsule to engage said first, male connector upon removal of the closure from said capsule.

8. The system of claim 7 wherein said first connector can rotate or oscillate a toothbrush head through an arc sufficient to promote oral hygiene.

9. The system of claim 7 further comprising a spindle/neck segment that includes said ejector mechanism.

* * * * *